United States Patent [19]

Wentzell

[11] Patent Number: 4,797,613
[45] Date of Patent: Jan. 10, 1989

[54] EXPANDABLE EDDY CURRENT PROBE FOR INSPECTING THE INTERIOR OF TUBULAR CONDUITS

[75] Inventor: Timothy H. Wentzell, South Windsor, Conn.

[73] Assignee: Combustion Engineering, Inc., Windsor, Conn.

[21] Appl. No.: 693,427

[22] Filed: Jan. 22, 1985

[51] Int. Cl.$^4$ .................... G01N 27/72; G01N 27/82; G01R 33/12
[52] U.S. Cl. .................................................. 324/220
[58] Field of Search ............................... 324/219–221; 33/178 E, 178 F

[56] References Cited

U.S. PATENT DOCUMENTS

| | | | |
|---|---|---|---|
| 3,808,696 | 5/1974 | Possati | 33/178 E |
| 4,137,639 | 2/1979 | Zumbach | 324/220 |
| 4,303,884 | 12/1981 | Malick | 324/220 |
| 4,306,455 | 12/1981 | Selleri | 33/178 F |
| 4,438,399 | 3/1984 | Schnabl et al. | 324/220 |
| 4,477,777 | 5/1984 | Sharp et al. | 324/220 |
| 4,530,161 | 7/1985 | Blankinship | 33/178 F |

*Primary Examiner*—Gerard R. Strecker
*Assistant Examiner*—Walter E. Snow
*Attorney, Agent, or Firm*—John H. Mulholland

[57] ABSTRACT

A probe (8) for inspecting the walls of a tubular conduit (40, 42) or the like is provided with a pair of movable arms (20a, 20b) urged outward from a central rod 4 into contact with the tube interior. Eddy current coils (16, 18) carried in the tube engaging ends (32a, 32b) of the arms (20a, 20b) are maintained in a constant, spaced apart relationship with the tube wall interior for increasing inspection accuracy and sensitivity. The movable arms (20a, 20b) can accommodate varying internal tube diameters, expanding and contracting relative to the central rod (4). A sloping nose (2) and tapered arm portions (32a, 32b) assist the probe in traversing the conduit interior.

2 Claims, 3 Drawing Sheets

EXPANDABLE EDDY CURRENT PROBE FOR INSPECTING THE INTERIOR OF TUBULAR CONDUITS

FIELD OF THE INVENTION

The present invention relates to an apparatus for inspecting the walls of a cylindrical conduit or the like, and more particularly, an apparatus for inspecting a conduit wall utilizing the induction of an eddy current within said wall to provide an indication of wall integrity.

BACKGROUND OF THE INVENTION

Inspection of tubes or other conduits for defects or wear within the walls is a necessary and time-comsuming task for owners and operators of processes and equipment wherein high pressure fluid is transferred. Although many techniques have been developed and used in the prior art for inspecting newly manufactured tubing, it is the inspection of installed tubing which presents the greatest challenge to those in the industry. This is due to two factors: the difficulty in accessing sections of the installed tubing which may be within a tube bank or pressure vessel, as well as the possibility that significant structural degradation is likely to have occurred after an extended period of operation under conditions of high pressure, high temperature, and/or corrosive environment.

One such application wherein inspection of the structural integrity of an installed tube is critical is in the steam generators of a nuclear powered electric generating plant. In such a plant, the heated primary coolant flows through a plurality of inverted U-shaped tubes immersed in water from which steam is generated.

As it is typical in such an application for the primary side coolant pressure to be higher than that of the secondary, steam producing side, it is apparent that a failure of a steam generator tube will cause a leakage from the primary coolant into the secondary system.

The occurrence of such leakage is not unusual in such units, especially after extended periods of operation. For this reason, inspection of the individual steam generator U tubes is performed at regular intervals while the plant is shut down for service. An effective test program will not only locate specific failures that have already occurred in the steam generator tubing, but also attempt to identify the specific locations where a failure may be likely to soon occur. Thus, a high accuracy and sensitivity in the testing apparatus is a very desirable feature and has been the goal of the test apparatus heretofore in use and well known in the prior art.

One method of sensing anomalies in a metal structure utilizes the electrical eddy currents set up when a magnetic field and a conductive metal structure are moved relative to each other. The electrical eddy currents induced by such movements may be monitored by a magnetic field sensor and the results analyzed to determine the condition of the inspected metal structure. To insure repeatability and accuracy, this method requires that the current inducing and sensing coils of the probe apparatus be maintained at a close and constant spacing to the surface of the metal being analyzed. For eddy current probes typically used in tubular heat exchangers as discussed hereinabove, the eddy current probe is placed within the interior of the tube being examined and moved longitudinally therethrough.

For tubing with a constant internal diameter, it is relatively straightforward to design an eddy current probe such as that shown in U.S. Pat. No. 4,438,399 to Schnabl et al. The coils of the probe may be maintained at a known spacing from the interior surface of the tube giving accurate and repeatable measurements. However, probes known in the prior art are not suited for use in conduits wherein the internal diameter may not be substantially constant along the length of the tube, as the probe must be designed to traverse the narrowest part of the conduit and may thus be loose or otherwise unsupported laterally in other, larger interior segments.

Situations such as this occur in the case of a previously failed nuclear steam generator tube which has been repaired by welding an internal sleeve over the site of the tube failure. Such internal sleeving results in a segment of the steam generator tube which is of significantly smaller internal diameter than that of the remainder of that particular tube but is not so restrictive as to significantly impair the flow of primary fluid therethrough. Tubes having sleeved sections still require the same careful inspection as do other, intact tubes, but have proved a problem for the probes of the prior art which are unable to both traverse the reduced diameter sleeved segment and give accurate and repeatable measurements of the tube condition in the remainder of the tube.

With the sleeving of failed tubes currently presenting an economically and technically beneficial alternative to the former practice of simply plugging off the failed tube in a nuclear steam generator, the need for an inspection apparatus which meets the rigorous inspection standards of the industry is readily apparent to those skilled in the art.

SUMMARY OF THE INVENTION

The present invention provides an expandable probe for examining the interior of a variable diameter tube wherein the probe includes a pair of opposing arms each radially pivotable about a pivot point on a central rod, each arm further having one end configured to fit closely against the interior surface of the tube and including means for detecting the presence of flaws or other anomalies in the tube wall.

The preferred embodiment of the present invention provides two pairs of said arms, each pair being pivotable in a plane normal to that of the other, for fully supporting the probe within the tube as the probe is moved longitudinally therethrough. The detecting means in the preferred embodiment includes four conductive coils disposed in the tube engaging ends of the arms for simultaneously inducing and monitoring electromagnetic eddy currents in the tube wall. Each coil is configured to scan a 120° radial segment of the tube wall, resulting in a complete, overlapping examination as the probe is pulled or pushed through the tube.

The pivotable arms are tensioned outward in the preferred embodiment by a strip of elastomer insuring close contact with the tube wall and supporting the probe as it traverses the length of the tube. When passing through sections of restricted tube internal diameter, such as an internally sleeved repair, the pivotable arms of the probe according to the present invention are able to accommodate the restricted inner diameter while still maintaining an optimum spacing between the sensing coil and the tube wall.

The present invention therefore provides a probe which is able to traverse a tube of varying internal diameter while maintaining a plurality of detecting means in optimum orientation and spacing with the tube wall.

It is further a feature of the probe according to the present invention to provide a device for scanning the entire tube circumference in one pass of the probe therethrough.

It is still further a feature of the probe according to the present invention to traverse and scan sleeved tube repairs wherein a sleeve section has been placed within a flawed tube to prevent leakage therefrom, causing the tube to have a reduced internal diameter in that segment of the tube which has been sleeved.

BRIEF DESCRIPTION OF THE DRAWING FIGURES

DESCRIPTION OF THE PREFERRED EMBODIMENT

Figure 1:
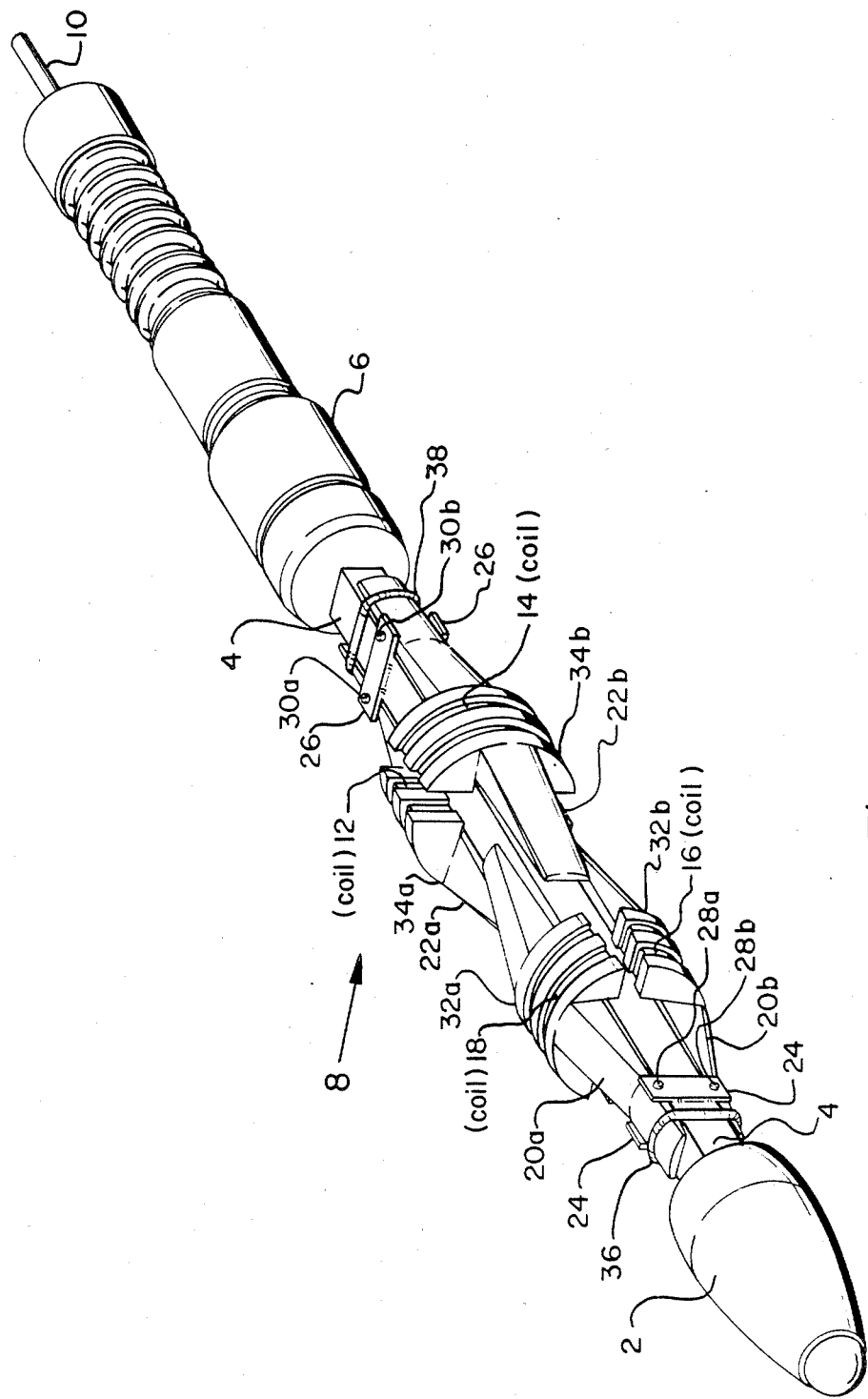
FIG. 1 shows an isometric view of the probe according to the present invention.

Referring now to the drawing figures, and in particular to FIG. 1, the preferred embodiment of the probe according to the present invention will now be described. A nose member 2 is shown secured to one end of an elongated central rod 4. The end of the central rod 4 opposite the nose member 2 is secured to a detachable connector 6 which allows the probe 8 to be detached from the guide wire 10 for replacement or service. In operation, the relatively stiff but flexible guide wire 10 is used to push and/or pull the probe through the tube being inspected. Guide wire 10 also carries any electrical conductors necessary for the operation of the eddy sensing coils 12, 14, 16, 18.

Between the nose member 2 and the connector 6 are two pairs of pivotable arms 20a, 20b and 22a, 22b shown supported relative to the central rod by respective pairs of pivot plates 24, 26. Each arm 20a, 20b, 22a, 22b is provided with a pivot point, 28a, 28b, 30a, 30b, respectively.

As can also be seen in FIG. 1, each pair of pivotable arms 20a, 20b and 22a, 22b move in a plane normal to that of the other pair. The coil carrying, or tube engaging, free ends 32a, 22b, 34a, 34b of the respective guide arms 20a, 20b, 22a, 22b, are each urged outwardly away from the central rod 4 by the compressive force exerted by the elastomeric bands 36, 38 on the lever ends of the respective pairs of guide arms 20a, 20b and 22a, 22b.

The tube engaging ends 32a, 32b, 34a, 34b of the respective guide arms 20a, 20b, 22a, 22b are thus seen to be constantly urged outward away from the central rod for the purpose of positioning the sensor coils 12, 14, 16, 18 near the inner surface of the inspected tube when the probe 8 is inserted therein. The elastomeric bands 36, 38 act to maintain this close positioning, without regard to small but significant variations in the inner tube diameter.

Figure 2:
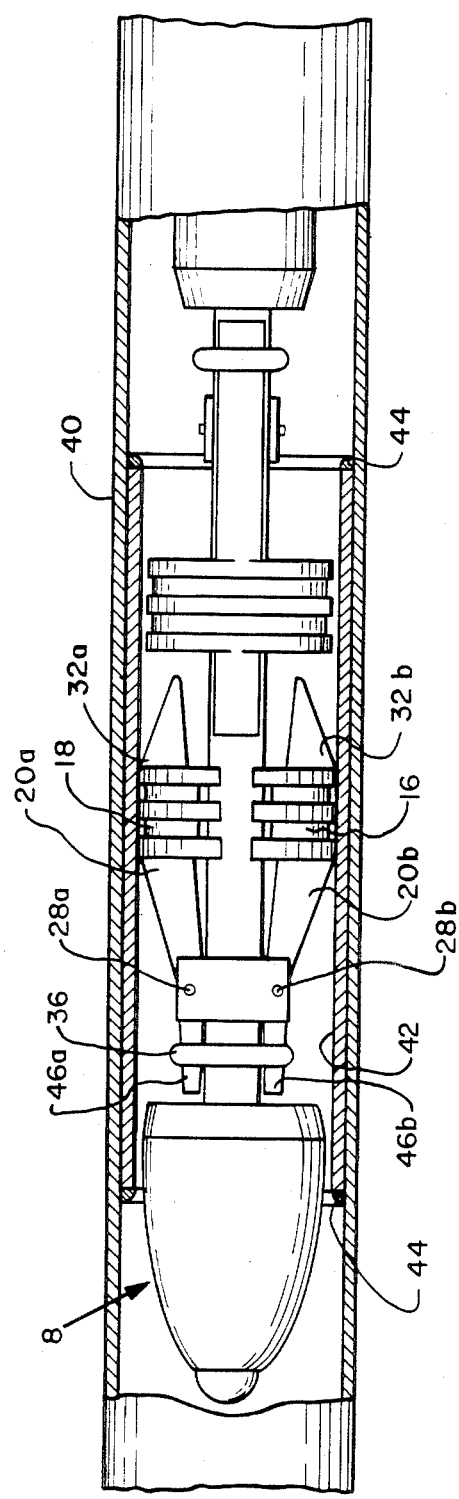
FIG. 2 shows a side view of the probe inserted into a sleeved tube segment.

Such a situation of varying tube diameter is shown clearly in FIG. 2 wherein the probe 8 is shown in the process of traversing an elongated metal tube 40. As shown in FIG. 2, the probe is currently passing through an interior tubular sleeve 42 which has been positioned within the outer tube 40 and annularly welded 44 at each end. This arrangement of tubes may commonly occur when a leak in the outer tube 40 has been detected and previously repaired such as in the steam generator of a nuclear electric generating facility.

It can be clearly seen by those skilled in the art that the tube engaging ends 32a, 32b of the first pair of opposing arms 20a, 20b are urged snugly against the inner surface of the sleeve tube 42 by the combined action of the elastomeric band 36, the pivot points 28a, 28b, and the lever ends 46a, 46b of the respective guide arms 20a, 20b. Eddy current sensing coils 16, 18 carried by the respective tube engaging ends 32b, 32a, are thus kept in close and constant proximity to the inner surface of the portion of the tube currently being inspected, resulting in an accurate and sensitive evaluation of the tube wall condition.

Figure 3:
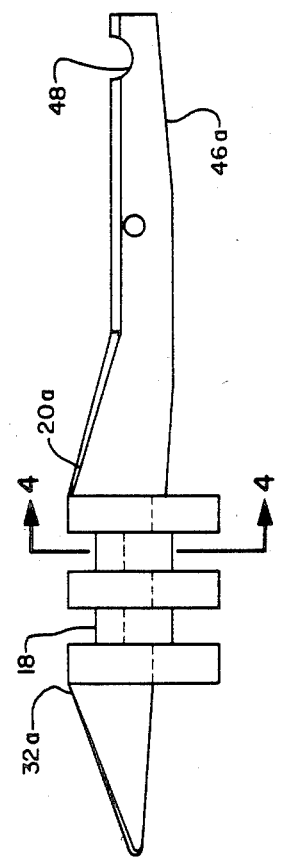
FIG. 3 shows a detailed view of a pivotable arm of the probe according to the present invention.

FIG. 3 shows a detailed view of a single guide arm 20a and the various parts thereof as previously described. Also shown more clearly in FIG. 3 is a small recess 48 in the lever end 46a for receiving the elastomeric band 36 and preventing displacement due to slippage or other action.

Figure 4:
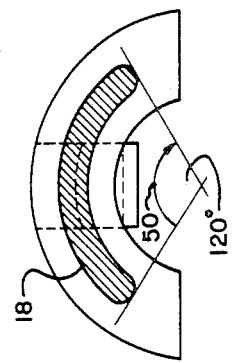
FIG. 4 shows a cross sectional view of the pivotable arm as indicated in FIG. 3.

FIG. 4 shows a cross section of the guide arm 20a as shown in FIG. 3. The sensing coil segment 18 is shown to scan a segment of the tube wall equivalent to a radial arc 50 of 120°. For the probe of the preferred embodiment having two pairs of arms oriented to pivot each in a plane normal to that of the other pair, and for individual guide arms each scanning a radial arc equal to 120°, it will be appreciated by those skilled in the art that the probe according to the preferred embodiment of the present invention is able to conduct a complete examination of the entire tube wall in a single longitudinal pass through the subject tube.

The completeness and accuracy of the tube inspection provided by the probe according to the present invention can greatly reduce the time spent in inspecting and therefore servicing the steam generators of nuclear electric power generating stations. Reduced maintenance time translates into reduced time off-line and increased plant productivity.

It is to be understood that the appended drawing figures and preceding discussion have been directed primarily toward the illustrative, preferred embodiment of the present invention and that other, equivalent embodiments utilizing functionally and/or structurally equivalent components which are or become apparent to those skilled in the art are also within the scope of the preceding disclosure and the following claims.

I claim:

1. A probe for longitudinally traversing the interior of an elongated, variable inner diameter installed steam generator tube, comprising:
    a central rod, opposing guide arms, each guide arm mounted on a pivot oriented transversely to the central rod at a fixed point intermediate the ends of the guide arm and each guide arm further including,
    a tube engaging guide arm free end configured to fit closely against a portion of the interior tube surface and an opposite guide arm lever end extending from the pivot point in a direction opposite the tube engaging end and terminating in a spaced apart relationship with the central rod;
    electrical sensor means disposed within the tube engaging free end, for detecting flaws in the tube wall currently adjacent the tube engaging end;

compression means acting radially inwardly on the opposite guide arm lever end of each of the guide arms for urging the tube engaging free end of the opposing guide arms outward from the central rod into supportive contact with the interior of said tube; and means for selectively moving the probe longitudinally through said installed steam generator tube.

2. The probe as recited in claim 1, wherein the means acting radially inwardly includes an elastomeric material.

* * * * *